United States Patent [19]

Ratner et al.

[11] Patent Number: 5,091,204
[45] Date of Patent: Feb. 25, 1992

[54] POLYMERIC INTRAOCULAR LENS MATERIAL HAVING IMPROVED SURFACE PROPERTIES

[75] Inventors: Buddy D. Ratner; Nancy B. Mateo, both of Seattle, Wash.

[73] Assignee: Weshington Research Foundation, Seattle, Wash.

[21] Appl. No.: 111,132

[22] Filed: Oct. 21, 1987

Related U.S. Application Data

[60] Division of Ser. No. 768,895, Aug. 23, 1985, abandoned, and a continuation-in-part of Ser. No. 41,796, Apr. 23, 1987.

[51] Int. Cl.$^5$ ............................ B05D 3/06; B05D 5/08
[52] U.S. Cl. ............................ 427/2; 427/38; 427/44; 427/164; 427/166; 623/6
[58] Field of Search ................... 427/2, 164, 38, 44, 427/166; 623/6; 264/14

[56] References Cited

U.S. PATENT DOCUMENTS

| | | | |
|---|---|---|---|
| 4,188,426 | 2/1980 | Auerbach | 427/40 |
| 4,655,770 | 4/1987 | Gupta et al. | 623/1 |
| 4,656,083 | 4/1987 | Hoffman et al. | 428/265 |
| 4,666,644 | 5/1987 | Tillay | 623/6 |
| 4,681,585 | 7/1987 | Sayano et al. | 623/6 |
| 5,034,265 | 7/1991 | Hoffman et al. | 427/2 X |

*Primary Examiner*—Evan Lawrence
*Attorney, Agent, or Firm*—Pravel, Gambrell, Hewitt, Kimball & Krieger

[57] ABSTRACT

A method of making an improved intraocular lens for implanting in the eye by coating a glass or polymeric lens substrate with a fluorocarbon polymer to produce a rigid, low-energy surface that will significantly reduce adhesion and damage to corneal endothelial tissues upon implantation. The preferred lens material is produced by exposing the lens substrate to a gas plasma of a fluorocarbon monomer.

17 Claims, 1 Drawing Sheet

POLYMERIC INTRAOCULAR LENS MATERIAL HAVING IMPROVED SURFACE PROPERTIES

This application is a division, of application Ser. No. 768,895, filed Aug. 23, 1985, abandoned, and is related to continuation-in-part application Ser. No. 041,796 which was filed Apr. 23, 1987.

DESCRIPTION

1. Technical Field

The field of the invention is biocompatible polymeric materials and the method of making such materials. More particularly, the invention relates to such polymers having modified surface properties that substantially improve suitability for intraocular implants.

2. Background of the Invention

Adhesive contact between the most commonly used intraocular lens material, poly (methyl methacrylate) (PMMA), and the corneal endothelium during surgical implantation results in the loss of endothelial cells which do not regenerate. Cell loss has been directly related to the number of times the intraocular lens contacts the endothelium during surgery, with approximately 20% loss resulting from each contact. The relationships between cell adhesion and polymer surface properties such as surface energy, surface chemistry and surface rigidity have been studied by many investigators. However, corneal endothelial cell adhesion has not been heretofore directly correlated with the properties of the intraocular lens materials examined.

Surface modification of the PMMA surface substrate has been shown to alter lens adhesiveness to cells. Investigators have used gamma radiation grafting to polymerize hydroxyethyl methacrylate (HEMA) and vinyl pyrrolidone (VP) onto a PMMA substrate. Using a laboratory "touch test" between the modified lens material and rabbit corneas, it was discovered that PMMA alone induces 10-30% damage, a PMMA/HEMA graft about 10% damage and a PMMA/VP graft less than 10% cell damage. However, these "touch tests" have been discovered to be relatively arbitrary and nonreproducible.

Another investigator used an 18 gram weight to press sample intraocular lens and rabbit cornea together for 10 seconds to produce a consistent force on the endothelium. It was reported that PMMA caused "considerable damage", silicone resin lenses induced "less damage" than PMMA, and silicone elastomer created "far less damage". No quantitative comparisons of cell damage between the samples were possible.

In yet another study, the investigator constructed and employed an instrument directly measuring the force of adhesion between rabbit corneal endothelium and intraocular material samples. The average stress calculated for PMMA was $0.66 \text{ g/cm}^2$ which was shown to be the highest of all materials studied. A plasma-deposited VP coating on PMMA and a conventional coating of Healon TM (manufactured by Pharmacia Inc.) on PMMA each lowered the stress to $0.19 \text{ g/cm}^2$. Two hydrogels poly (HEMA) and Duragel TM (Soflex), exhibited the lowest stresses, 0.09 and $0.14 \text{ g/cm}^2$ respectively of the materials tested.

Thus, prior workers have modified PMMA surface properties by coating with a number of materials such as HEMA and VP. They have discovered that such coatings reduce cell damage to values below that measured for the conventional PMMA intraocular lens material. The best state-of-the-art coatings appear to result from surfaces that are soft, hydrophilic hydrogels.

Hydrogels such as HEMA and VP demonstrate low cell damage relative to the PMMA substrate and other coatings tried. However, the hydrogels exhibit a number of disadvantages. For example, the coatings are soft and easily damaged. They are difficult to package and difficult to hydrate properly at surgery. Further, hydrogels are prone to calcification and bacterial contamination.

SUMMARY OF THE INVENTION

It is an object of the invention to provide a surface-modified polymer that has improved biocompatibility and the method of making the same. It is particularly, an object of the invention to provide a surface modified poly (methyl methacrylate) intraocular lens that causes a reduction in adhesion damage of corneal endothelium cells during surgical implantation.

It is an object of the invention to provide an improved, modified intraocular lens material which includes a rigid, low-energy surface having reduced adhesion characteristics with corneal cells.

The improved intraocular lens material of the invention is an intraocular lens material polymer substrate including a fluorocarbon polymer coating bound covalently to the substrate. The fluorinated coating will protect the lens from degradation by the body by virtue of the dense and impermeable cross-linked nature of the film coating. Also, the fluorinated film will protect leaching of fusible components from the lens into the body.

The preferred intraocular lens material is a poly (methyl methacrylate) substrate including a fluorocarbon polymer coating. The surface coating is deposited by exposing the substrate polymer to a gaseous monomer and an electrical field. The field ionizes the monomer gas, creating a fluorocarbon plasma. The plasma reacts with the polymer substrate resulting in the simultaneous deposition and polymerization of the fluorocarbon groups and their attachment onto the substrate surface.

The preferred process for making a modified polymeric intraocular lens material includes placing poly (methyl methacrylate) substrate material in a chamber including a gaseous perfluoropropane monomer. A radio-frequency generator then induces an oscillating electric field within the chamber polymerizing the monomer and attaching it to the surface of the substrate. System parameters such as RF power, system pressure and length of reaction control the nature and depth of the deposition as desired.

BEST MODE FOR CARRYING OUT THE INVENTION

The surface modified intraocular lens material of the invention was produced by coating disks of a substrate polymer, poly (methyl methacrylate), with a fluorocarbon material. In the preferred process, deposition was accomplished by exposing the substrate to a gas plasma of perfluoropropane.

The plasma reactor was of conventional design including a glass chamber for holding the substrate material to be treated. The chamber was surrounded by capacitance plates coupled to a radio frequency generator which established an oscillating electric field within the chamber.

In operation, the sample disks of substrate material were placed in the chamber. The samples were then etched by exposure to an argon plasma. The samples were then exposed to a plasma of the monomer to be deposited on the substrate surface. In addition to the perfluoropropane monomer of the invention, tests were run using ethylene oxide (EO), N-vinyl-2-pyrrolidone (NVP) and hydroxyethyl methacrylate (HEMA). System parameters of RF power, chamber pressure and reaction time were varied to control the nature of the reaction and depth of depositions. Parameters selected depended upon the character of each monomer tested.

The resulting products were characterized in terms of surface chemistry and surface energy. Cell damage resulting from contact of the sample of the material of the invention with corneal tissue was measured and compared with the untreated substrate and other treated surfaces. The measured surface characteristics of the material of the invention as a function of cell damage were compared with measurements of the same qualities for the other surfaces.

Electron Spectroscopy for Chemical Analysis (ESCA) was used to determine elemental composition and bonding states of the outermost 100 Angstroms of the polymer surface. A survey scan at 1-1000 eV was taken to determine the various elements present. Then, scans in specified eV ranges were made to obtain the spectra of the elements C, O, F and N.

As a means of characterizing the surface energy of the material of the invention and comparable materials, the "critical surface energy" was determined using the method of Zisman, as described in "Relation of the Equilibrium Contact Angle to Liquid and Solid Constitution", *Advances in Chemistry Series No. 43*, Fowkes, Editor, American Chemical Society, Washington, D.C. pp. 1-51 (1964). The analysis required measuring contact angles of various purified liquids on each type of surface at atmospheric conditions. Cosines of the measured angles were then plotted as a function of the surface tensions of the test liquids, resulting in a Zisman plot from which the critical surface energy was calculated.

Actual interaction of the modified surface of the invention with corneal endothelium was determined by employing an apparatus which produced consistent and quanitatively comparable results between samples.

Figure 1:
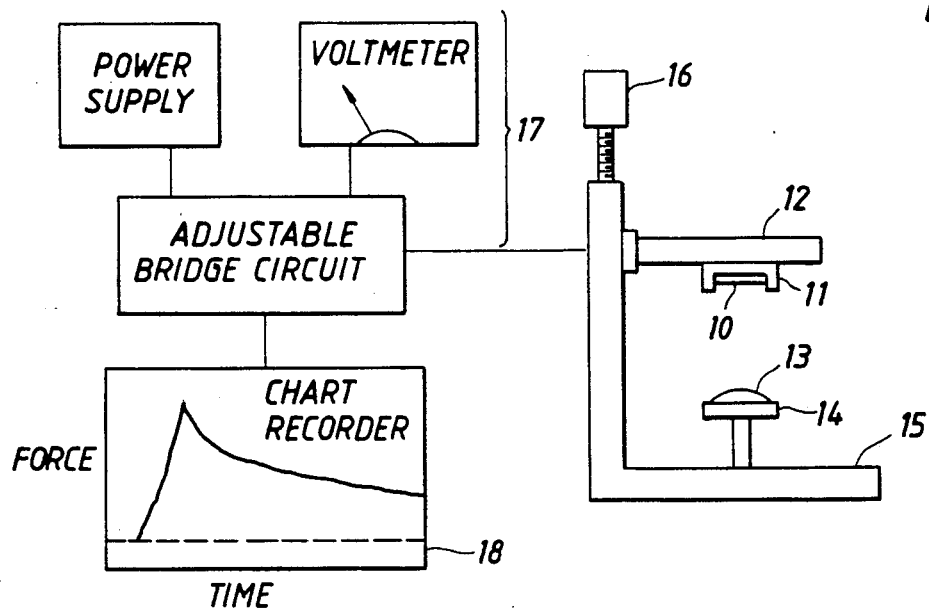
FIG. 1 is a schematic diagram of an instrument for contacting treated intraocular lens material with corneal tissue.

Referring to FIG. 1, the device used in this test is shown schematically. A disk 10 of the material to be tested is secured in a holder 11 mounted on the lever arm 12 of a microforce detector 17. A freshly excised rabbit cornea 13 is mounted in a holder 14 on a base 15 opposed to the disk 10 to be tested. A micrometer 16 is provided to advance the lever arm 12 and, the disk sample 10 into contact with the corneal button 13 at a measurable force. An electronic circuit of the microforce detector 17 measures the contact force, reporting the measurement on a chart recorder 18.

In operation the test disk 10 was brought into contact with the corneal tissue by means of the micrometer for a period of 40-60 seconds. The initial maximum force under which contact was made was recorded. The corneal buttons were then removed, stained and examined under a low power microscope. The percent damaged cells were counted and recorded.

The details of the process and results achieved are reported in the following examples.

EXAMPLE 1

PMMA lens material, PERSPEX TM fabricated by CooperVision of Seattle, Wash., in the form of 10mm diameter disks was selected. Monomers of perfluoropropane and ethylene oxide both manufactured by Matheson Chemical Company of Newark, Calif., N-vinyl-2-pyrrolidone manufactured by Alfa Products of Danvers, Mass. and hydroxyethyl methacrylate manufactured by Hydron Industries were prepared.

Sample disks were placed approximately 6 cm downstream of the capacitance plates and the continuous system was evacuated at 0.035 Torr. Argon was introduced at 0.25 Torr. RF generator power at 50 watts was continued for five minutes to allow etching of the PMMA substrate. After evacuating the reactor, the fluorocarbon monomer gas was introduced at the desired pressure. For perfluoropropane monomer pressure was 0.25 Torr and generator power was at 30 watts for 10 minutes. Afterwards, the chamber was evacuated to 0.035 Torr and then gradually brought up to the atmospheric pressure by introduction of Argon and air.

Two ESCA spectrometers, a Hewlett Packard Model 5950-B at University of Utah and a Surface Science Model SSX-100 at University of Washington were used to determine the chemical nature of the surfaces of the intraocular lens material samples. Spectra from the HP-5950-B were resolved using a DuPont 310 curve resolver, while spectra from the SSX-100 were resolved with a peak-fitting routine on an HP-9836-C computer. The C(1s) hydrocarbon peak was assigned to 285 eV and used as a reference peak to correct for any energy shifts. The ESCA results of the samples measured appear in section 2 of the following table.

TABLE 1

Elemental and Bonding Ratios

1. Stoichiometry based on monomer structure

| Compound | C/O | C/N | C/F | CH | C—O | C=O | $\overset{O}{\underset{\|}{C}}$—O | C—N | $\overset{O}{\underset{\|}{C}}$—N |
|---|---|---|---|---|---|---|---|---|---|
| PMMA | 2.5 | — | — | 60 | 20 | — | 20 | — | — |
| HEMA | 2.0 | — | — | 50 | 33.3 | — | 16.7 | — | — |
| NVP | 6.0 | 6.0 | — | 50 | — | — | — | 33.3 | 16.7 |
| Ethylene Oxide | 2.0 | — | — | — | 100 | | | | |
| Perfluoropropane | — | — | 0.375 | CF$_3$ 33.3 | CF$_2$ 33.3 | CFCF$_n$ — | | CF 33.3 | C—CF$_n$ |

2. ESCA Results

TABLE 1-continued

| Compound | C/O | C/N | C/F | CH | C—O | C=O | $\overset{O}{\underset{\|}{C-O}}$ | C—N | $\overset{O}{\underset{\|}{C-N}}$ |
|---|---|---|---|---|---|---|---|---|---|
| PMMA | 3.0 | — | — | 58 | 23 | — | 19 | — | — |
| pHEMA (a) | 2.4 | — | — | 46 | 38 | — | 16 | — | — |
| HEMA (b) | 2.2 | — | — | 46.5 | 31 | — | 23.5 | — | — |
| pNVP (c) | 8.0 | 8.0 | — | 43.2 | — | — | — | 29.7 | 27.1 |
| NVP (b) | 5.7 | 3.1 | — | 53 | — | — | — | 34 | 13 |
| Ethylene Oxide (b) | 4.8 | — | — | 61 | 21 | 9 | 9 | — | — |
| | | | | | CF$_3$ | CF$_2$ | CFCF$_n$ | CF | C—CF$_n$ |
| Perfluoropropane (b) | — | — | 0.52 | 4.0 | 28.0 | 27.6 | 15.6 | 13.3 | 11.5 |

Notes
(a) Poly(HEMA) spun on glass coverslips (2% in DMF).
(b) Plasma-deposited film on PMMA disk.
(c) Poly(NVP) spun on glass coverslip (2% in methanol).

The contact angles of various purified liquids on each type of surface were measured under atmospheric conditions using a Rame-Hart goniometer, Model 110-00-00NRL Experimentally determined values of the critical surface energy $\gamma_c$, for the several surfaces tested are presented in Table II. Teflon ™ and Mylar ™ were examined as reference surfaces.

TABLE II

| Critical Surface Tensions ($\gamma_c$) of Solid Surfaces | |
|---|---|
| Surface | $\gamma_c$ (ergs cm$^{-2}$) |
| Teflon ™ (TFE) | 20.0 ± 1.3 |
| Mylar ™ | 46.7 ± 0.3 |
| PMMA | 37.8 ± 3.2 |
| Perfluoropropane film | 8.1 ± 3.1 |
| Ethylene Oxide film | 45.4 ± 2.7 |
| HEMA film | 49.4 ± 4.1 |
| NVP film | 48.0 ± 4.3 |

EXAMPLE 2

The samples produced and characterized in Example 1 were contacted with corneal tissue by means of the apparatus of FIG. 1.

Each cornea, rimmed by 2-3 mm of sclera, was excised from a 2-3 kg New Zealand white rabbit and immediately placed in RPMI 1640 media with HEPES buffer, L-Glutamine, and penicillin-streptomycin (Grand Island Biological). The cornea in solution was placed in a Forma Scientific Hydrojac CO$_2$ incubator for at least 30 minutes. In preparation for a test, the cornea was removed from this solution, rinsed in a 0.9% NaCl solution, placed on a concave Teflon ™ block, and trephined to form a 9-mm-diameter button. The cornea was then placed endothelial side up, in a convex stainless steel holder of the apparatus of FIG. 1. A circle of endothelium 7 mm in diameter was exposed with the center projected 2 mm above the level of the holder edge. A 0.9% NaCl solution was dropped intermittently onto the cornea to keep the cells continuously moist.

A 10-mm-diameter sample disk was mounted in the stainless steel holder of the apparatus which clamped the edges, leaving a 9-mm-diameter exposed planar surface. This holder was then attached to the micro-force detector 12, Deflection Sensor Cartridge, Model DSC3, manufactured by Imperial Controls. The system was calibrated using 1-20 gram weights, depending on the force anticipated for each test. The test range was: 4000-20,000 dynes.

The corneal holder was placed directly beneath the lens sample, and the two surfaces were brought into contact with the micrometer attachment. After 40-60 seconds, the cornea and the sample were separated. The cornea was immediately placed in a 0.9% NaCl solution. The initial and maximum force with which contact was made was recorded. Controls for the test were corneal buttons which remained in the holder for 20 minutes and were kept moist with 0.9% NaCl solution. These corneas were subjected to all handling except for actual contact with a sample disk.

To inspect the endothelium, the staining method of Spence and Peyman, described in "A New Technique for the Vital Staining of The Corneal Endothelium," *Invest. Ophtalmol*, 15, No.12 (1000) 1976, involving a combination of Trypan Blue and Alizarin Red S stains provided by Sigma Chemical of St. Louis, Mo. was used. The cornea was then examined under a low power X100 microscope. A central 9 cm$^2$ area, divided into 900 grids, was observed consistently for each cornea. The undamaged and damaged cells were counted.

The PMMA substrate and the treated disk were measured for cell damage over a range of contact forces. The results were then plotted showing cell damage as a function of contact force. Table III reports the best fit curves for the data for each sample. The data are also plotted in FIG. 2.

TABLE III

| | Best Fits for Cell Damage Data | | |
|---|---|---|---|
| Surface | Slope | Intercept | Average |
| PMMA | 0.00190 ± 0.000494 | −1.65 ± 5.4 | — |
| HEMA | 0.000498 ± 0.000190 | 1.99 ± 2.2 | — |
| NVP | 0.000646 ± 0.000239 | 1.27 ± 2.7 | — |
| Ethylene Oxide | 0.001240 ± 0.000565 | 17.44 ± 6.1 | — |
| Perfluoropropane | — | — | 6.96 ± 3.83 |

Referring to Table I of Example 1, the ESCA results of both conventional and plasma deposited polymers are compared with stoichiometry of the monomers. The untreated PMMA disk exhibits C/O ratios close to the expected ratio from stoichiometry. The types of bonding present in the sample also compare closely. Each of the HEMA and NVP plasma-deposited coating shows a close resemblance in composition and bonding to the stoichiometry and to the model poly(HEMA) and poly (NVP) conventional films spun on glass. The peaks comprising the ESCA spectra of the conventional HEMA and NVP polymer surfaces are more distinct than those in the spectral envelopes of the plasma-deposited films. The more ill-defined spectra of the plasma-deposited films reflect the wider distribution of structures, the increased number of chemical species, and the increased crosslinking, all of which are characteristic of plasma depositions. However, the similarity of these plasma deposits to the conventional polymers may indicate a higher level of molecular polymerization (i.e. free radical polymerization through the double bond) than atomic polymerization. This similarity also suggests a comparable regularity of structure which is important to the hydrogel character of conventional poly(HEMA) and poly(NVP). Hence, the coatings deposited by the HEMA and NVP plasma exhibit hydrogel behavior.

Coatings deposited by ethylene oxide and perfluoropropane plasmas are vastly altered from the monomer structures. These plasmas undergo complex reactions involving "atomic polymerization", a type of deposition in which the molecular structure of the monomer is not retained in the polymer. As a result, a regularity in the structure of the ethylene oxide plasma coating is not likely to occur because the bonding environments noted by ESCA are so dissimilar to those in conventional poly-(ethylene oxide).

Referring to Table II of Example 1, the plasma-altered surfaces exhibit definite changes in wettability compared to the PMMA substrate. The fluorinated plasma rendered the disk nonwettable. The other three plasma-deposited surfaces show an increase in wettability as the critical surface tension increases. These results are consistent with the trends reported in the literature, to the effect that wettability decreases with an increase in fluorination and increases with an increase in nitrogen or oxygen bonded to carbon.

Figure 2:
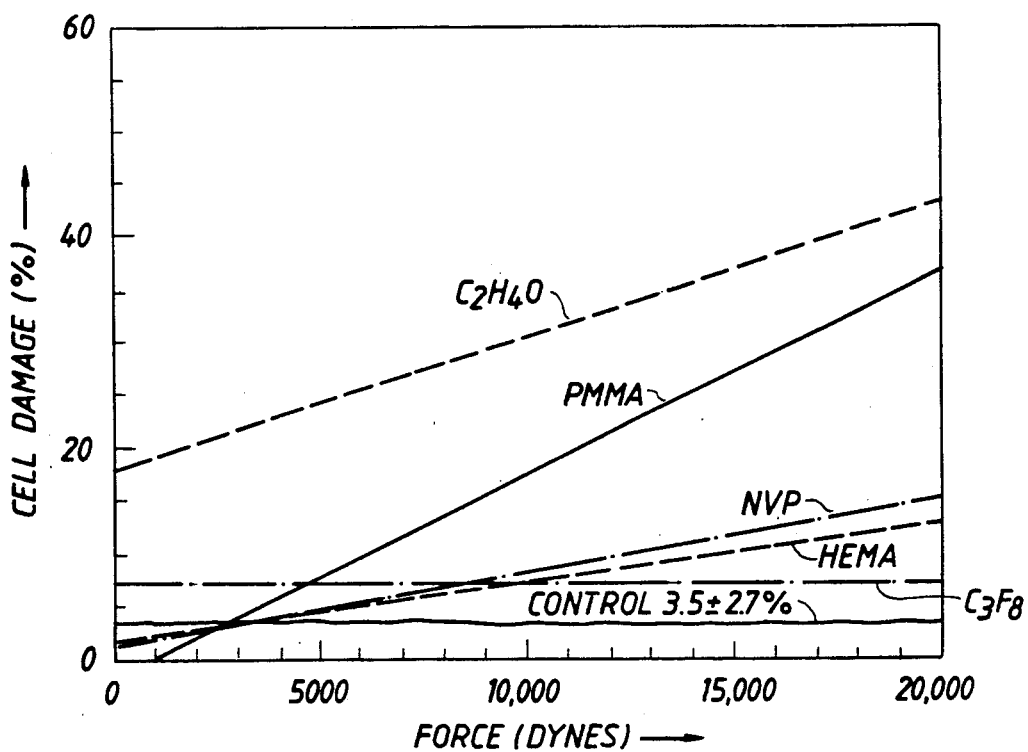
FIG. 2 presents percent corneal cell damage as a function of initial force of contact with tested intraocular lens materials.

In FIG. 2, percent cell damage is plotted as a function of initial force for each type of surface contacted with corneal tissue by means of the apparatus shown in FIG. 1 and described in Example 2. The solid horizontal line at 3.5±2.7% represents the average damage associated with the control corneas. The lines shown for the other samples are the best curves for the force-damage data, representing either a least squares fit or an average of cell damage where damage appears independent of force. Table III reports the parameters and errors of the fits of these data.

The choice of fit was based on results from the "f test for chi-square" which determines whether adding a term dependent on force (least squares line) is an improvement from the average damage line. PMMA, ethylene oxide, NVP and HEMA surfaces displayed a trend of increasing damage with increasing force, and the least squares fits were plotted. Since the slope of the perfluoropropane force-damage curve was not significantly different from zero, the average cell damage value was plotted.

The parameter values shown in Table III were used to calculate the significance of the differences in the cell adhesion associated with the five surfaces. Relative to PMMA, each of the four data sets was found to have greater than 97% probability that the difference between the fit for PMMA and for an altered surface fit is significant.

The fluorinated surface of the invention induced the lowest endothelial damage over the entire force range investigated. Damage appears to be independent of force.

The HEMA and NVP surfaces were also associated with decreased cell damage, compared to the unmodified PMMA. However, both HEMA and NVP surfaces induced increasing cell damage with increasing force.

The ethylene oxide coating caused significantly greater adhesion damage to the cornea than PMMA.

As shown, the degree of cell adhesion damage is significantly changed by modifying the PMMA surface. Changes in the surface chemistry and surface energy have been documented by the ESCA and contact angle studies reported in Example 1.

In summary, the data demonstrate a change in surface properties of poly (methyl methacrylate) material modified by RF plasma deposition. The degree of endothelial cell adhesion to the surface is considerably altered. The percent cell damage as a function of the initial force of contact for each modified surface was significantly different than that induced by PMMA. The results suggest that a rigid, low-energy fluorinated surface is desirable for reduced cell adhesion.

Any glass or polymeric substrate for which low-cell adhesion properties are desired and upon which a fluorocarbon monomer may be plasma deposited can be improved by modifying its surfaces according to this invention. Such substrates include glass, polypropylene and silicone polymers, for example. Fluorocarbon monomers or mixtures thereof which can be deposited on a substrate using the gas plasma technique are within the scope of the invention. Preferred monomers include perfluoropropane, perfluoropropene, hexafluoroethane, and tetrafluoroethylene, for example.

We claim:

1. A method for making an intraocular lens that causes low corneal endothelical cell damage during implantation, comprising:
   selecting a substrate for an intraocular lens; and
   applying a fluorocarbon polymer coating to said substrate prior to insertion of the intraocular lens into the eye,
   wherein said applying step includes binding said fluorocarbon polymer coating to said base material by plasma deposition of a gaseous fluorocarbon monomer.

2. A method of making an intraocular lens for implantation in an eye without substantial risk of corneal endothelial cell damage, comprising:
   providing an intraocular lens substrate, and
   coating the substrate with an impermeable layer of fluoropolymer thereby forming a rigid, low-energy surface thereon,
   wherein said fluoropolymer coating is applied by exposing the substrate to a gaseous fluorocarbon monomer or mixtures of such monomers, in an atmosphere including radio-frequency generated energy such that a plasma is created, causing the monomer to bind to the substrate and polymerize.

3. The method of claim 2 wherein said substrate is a glass material.

4. The method of claim 2 wherein said substrate is a polymeric material.

5. The method of claim 2 wherein said fluoropolymer coating is a dense, impermeable, cross-linked fluorocarbon film.

6. The method of claim 2 wherein said monomer is perfluoropropane.

7. The method of claim 2 wherein said substrate is poly(methyl methacrylate.

8. The method of claim 2 wherein said fluoropolymer is poly(perfluoropropane).

9. The method of claim 2 wherein said fluoropolymer is a fluorinated hydrocarbon.

10. A method of making an intraocular lens for implantation in an eye without substantial risk of corneal endothelial cell damage, comprising:

providing an intraocular lens substrate, and coating the optic portion with an impermeable layer of fluoropolymer thereby forming a rigid, low-energy surface thereon, said coating step including contacting the substrate with a gaseous plasma generated by a radio-frequency discharge, the plasma containing at least one fluorocarbon monomer, whereby the monomer is polymerized on the surface of the substrate.

11. The method of claim 10 wherein said monomer is perfluoropropane.

12. The method of claim 10 wherein said substrate is poly(methyl methacrylate).

13. A method of making an intraocular lens for implantation in an eye without substantial risk of corneal endothelial cell damage, comprising:

providing an intraocular lens substrate, and coating the substrate with an impermeable layer of fluoropolymer thereby forming a low-energy fluorinated surface, thereon, said coating step including exposing the substrate to a fluorocarbon monomer and an electric field which ionizes the monomer, forming a plasma gas of the monomer which polymerizes and covalently bonds to the base material of the substrate.

14. The method of claim 13 wherein said gas plasma deposition is by means of a radio-frequency generated discharge.

15. The method of claim 13 wherein said gas plasma deposition is by means a microwave generated discharge.

16. The method of claim 13 wherein the fluorocarbon monomer is selected from the group consisting of perfluoropropane, perfluoropropene, hexafluoroethane, tetrafluoroethylene and mixtures thereof.

17. A method of making an intraocular lens for implantation in an eye without substantial risk of corneal endothelial cell damage, comprising:

providing an intraocular lens substrate, the substrate being selected from the group consisting of glass, poly(methyl methacrylate), polypropylene and silicone polymers; and coating the substrate with an impermeable layer of a fluoropolymer thereby forming a surface thereon, wherein the layer of fluoropolymer is formed from a plasma gas produced by the ionization of at least one fluorocarbon monomer in an electric field.

* * * * *